United States Patent
Jacobson et al.

(10) Patent No.: US 10,848,389 B2
(45) Date of Patent: *Nov. 24, 2020

(54) AUTO-PRIORITIZATION OF DEVICE TRAFFIC ACROSS LOCAL NETWORK

(71) Applicant: Google LLC, Mountain View, CA (US)

(72) Inventors: Alex Daniel Jacobson, Mountain View, CA (US); Laura Marie Eidem, Mountain View, CA (US)

(73) Assignee: Google LLC, Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/707,533

(22) Filed: Dec. 9, 2019

(65) Prior Publication Data

US 2020/0119999 A1 Apr. 16, 2020

Related U.S. Application Data

(63) Continuation of application No. 15/392,576, filed on Dec. 28, 2016, now Pat. No. 10,536,345.

(51) Int. Cl.
*H04L 12/24* (2006.01)
*H04L 12/911* (2013.01)
(Continued)

(52) U.S. Cl.
CPC ............ *H04L 41/16* (2013.01); *G16H 40/63* (2018.01); *G16H 50/30* (2018.01);
(Continued)

(58) Field of Classification Search
CPC ....................................................... H04L 41/16
See application file for complete search history.

(56) References Cited

U.S. PATENT DOCUMENTS 7,460,476 B1 12/2008 Morris
8,854,966 B2 10/2014 Fadell
(Continued)

FOREIGN PATENT DOCUMENTS

EP 2521312 11/2012

OTHER PUBLICATIONS

Chaudhary et al.. "Flow classification using Clustering and association rule mining," 15th IEEE International Workshop on Computer Aided Modeling, Analysis and Design of Communication Links and Networks, Dec. 3, 2010, 5 pages.
(Continued)

*Primary Examiner* — Adnan M Mirza
(74) *Attorney, Agent, or Firm* — Honigman LLP; Brett A. Krueger (57) ABSTRACT

Methods, systems, and apparatus, including computer programs encoded on a computer storage medium, for prioritizing network traffic. In one aspect, a method includes collecting, for local networks, traffic data representing communication traffic over the local network for a period of time; determining, for each of the network devices included in the networks, a device type of the network device and at least one device priority value for the network device; training a device prioritization model, using the traffic data and the device priority values of the devices, receiving, by the device prioritization model, for a local network, a list of network devices that are included in the local network; and generating, by the device prioritization model, a prioritization scheme for the local network that prioritizes device traffic among the network devices based on the device types and device priority values of the network devices.

18 Claims, 5 Drawing Sheets

(51) Int. Cl.
*H04L 12/927* (2013.01)
*G16H 40/63* (2018.01)
*H04L 29/08* (2006.01)
*H04L 12/26* (2006.01)
*G16H 50/30* (2018.01)
*H04L 12/28* (2006.01)

(52) U.S. Cl.
CPC ...... *H04L 12/2803* (2013.01); *H04L 41/0823* (2013.01); *H04L 41/0853* (2013.01); *H04L 41/145* (2013.01); *H04L 41/147* (2013.01); *H04L 43/0882* (2013.01); *H04L 47/805* (2013.01); *H04L 47/821* (2013.01); *H04L 67/12* (2013.01); *H04L 43/08* (2013.01)

(56) References Cited

U.S. PATENT DOCUMENTS

| | | |
|---|---|---|
| 10,536,345 B2 | 1/2020 | Jacobson et al. |
| 2003/0193395 A1 | 10/2003 | Ahiska et al. |
| 2016/0134474 A1 | 5/2016 | Stassner |

OTHER PUBLICATIONS

International Search Report and Written Opinion issued in International Application No. PCT/US2017/068496, dated Feb. 27, 2018, 19 pages.

PCT Written Opinion issued in International Application No. PCT/US2017/068496, dated Nov. 16, 2018, 7 pages.

Sayuti et al. "Lightweight Priority Scheduling Scheme for Smart Home and Ambient Assisted Living System," International Journal of Digital Information and Wireless Communications, 2014, 4.1: 114-123.

AUTO-PRIORITIZATION OF DEVICE TRAFFIC ACROSS LOCAL NETWORK

CROSS-REFERENCE TO RELATED APPLICATIONS

This application is a continuation application of, and claims priority to, U.S. patent application Ser. No. 15/392,576, titled "AUTO-PRIORITIZATION OF DEVICE TRAFFIC ACROSS LOCAL NETWORK," filed on Dec. 28, 2016. The disclosure of the foregoing application is incorporated herein by reference in its entirety for all purposes.

BACKGROUND

The "Internet of Things" (IoT) refers to internetworked physical devices that are embedded with electronics, software, and other system components that enable the objects to collect, exchange and process data. Such devices include not only computers, but phones, appliances (refrigerators, washers, dryers, etc.), security monitoring equipment, health monitoring equipment, gaming devices, and any other device for which interconnectivity may be utilized. As more appliance and home devices of the IoT are added to residential and commercial properties, bandwidth for device traffic for these devices becomes competitive. This may result in delays, dropped packets, and device processing errors.

Some network linking devices, such as routers or gateways, allow users to prioritize traffic among devices. For example, device addresses, such as MAC addresses or even IP addresses, can be selected and traffic priorities for those devices. However, many users do not know how to manage network liking devices to implement such manual prioritization schemes. Moreover, those users that can prioritize device traffic on local networks within a residence or a building must, by much trial and error, implement multiple different prioritization schemes to determine which one provides an optimized quality of service (QoS) for particular devices without adversely impacting the QoS of other devices. Additions of devices to a network may require re-prioritization of traffic, which, in turn, leads to periods of inefficient network bandwidth utilization.

SUMMARY

This specification describes technologies relating to auto-prioritizing devices in local networks.

In general, one innovative aspect of the subject matter described in this specification can be embodied in methods that include the actions of collecting, for each of a plurality of local networks, each local network being a network that communicates with other networks through a network linking device and including a respective plurality of network devices that communicate through the network linking device, traffic data representing communication traffic over the local network for a period of time; determining, for each of the network devices included in the plurality of networks, a device type of the network device and at least one device priority value for the network device based on the device type, each device priority value being a measure of a priority of device traffic for the network device relative to other device traffic of other network devices; and training a device prioritization model, using the traffic data and the device priority values of the devices, for prioritizing network traffic for each network device in a local network. The method may optionally include receiving, by the device prioritization model, for a local network, a list of network devices that are included in the local network; and generating, by the device prioritization model, a prioritization scheme for the local network that prioritizes device traffic among the network devices based on the device types and device priority values of the network devices. Other embodiments of this aspect include corresponding systems, apparatus, and computer programs, configured to perform the actions of the methods, encoded on computer storage devices.

Particular embodiments of the subject matter described in this specification can be implemented so as to realize one or more of the following advantages. A device prioritization model can be trained employing machine learning to contextually understand when user devices tend to be most used in relation to a set of user devices in a local network. This may yield a more efficient use of network bandwidth, reducing the outlay requirements for network resources. Additionally, the model can adjust the prioritization of network traffic for different time periods (e.g., days of the week, times of the day, and holiday events, etc.). The use of the model to generate a prioritization scheme based on an input list of devices obviates the need for a rule-based approach that would require pre-defined sets of devices and require a large database of rules for multiple different types of device combinations. Moreover, the use of the model allows for prioritization schemes that are emergent and that would otherwise not be discovered by users. Additionally, by prioritization of devices, congestion that may occur when devices tend to synchronize overhead traffic is reduced, as the devices, based on the prioritization scheme, will end up reporting at different times. This results in a better utilization of available bandwidth.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Overview

A system generates a machine-learned model that auto-prioritizes devices in local networks. As used in this specification, a local network is a network that communicates with other networks through a network linking device and includes a respective set of network devices that communicate through the network linking device. The model is trained using observed network traffic and device prioritizations. Once trained, the model can be used to automatically prioritize network devices in a particular local network.

To train the model, the system collects, for multiple different local networks, traffic data that represents communication traffic over the local network for a period of time. The system then determines, for each of the network devices included in the local networks, a device type of the network device and a device priority value for the network device based on the device type. The device priority value is a measure of a priority of device traffic for the network device relative to other device traffic of other network devices based on the device type. Using the traffic data and the device priority values of the devices, the system then trains a prioritization model. Once the model is trained, it may receive a list of devices for a local network, and, based on the list, a prioritization scheme for the local network that prioritizes device traffic among the network devices based on the device types and device priority values of the network devices. In some implementations, the prioritization scheme may prioritize traffic of device based on the device priority value. In other implementations, the model may generate a traffic priority value for a particular device, where each traffic priority value is a measure of priority of the device's device traffic of a particular type. For example, a "System OK" reporting message for a medical device may have a traffic priority value that is less than a traffic priority value for a message from the medical device that is reporting the detection of a medical event.

In operation, the model receives a list of network devices that are included in a local network and provides the list of devices to the device prioritization model. The device prioritization model then generates a prioritization scheme for the local network that prioritizes device traffic among the network devices based on the list of network devices and the device priority values. The prioritization scheme, in the implementations that generate traffic priority values, generates, for each device in the list of devices, one or more traffic priority values. The prioritization scheme can then be applied to the network devices included in the local network.

These features and other features will be described in more detail below.

Example Operating Environment

Figure 1:
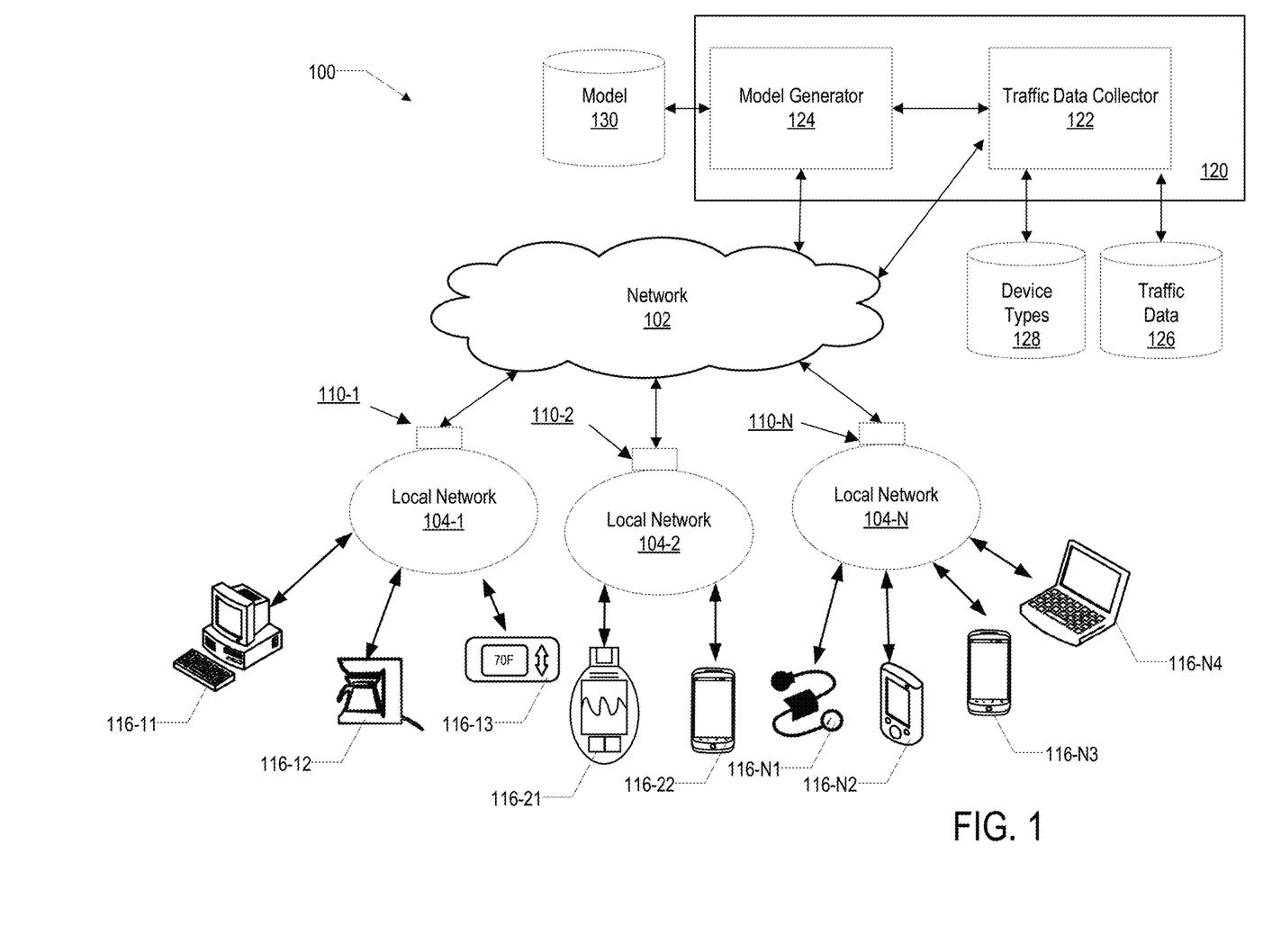
FIG. 1 is a block diagram of an example environment in which a device prioritization model is trained.

FIG. 1 is a block diagram of an example environment 100 in which a device prioritization model is trained. The environment includes a computer network 102, such as the Internet. The example environment may include many different local networks 104 (e.g., 104-1, 104-2 . . . 104-N) in communication with the network 102 through respective routers or gateways, which are generally referred to as network linking devices 110 (e.g., 110-1, 110-2, 110-N). Each local network has a collection of network-connected devices 116 in communication with their respective local networks 104-1, 104-2 . . . 104-N, (e.g., 116-11 and 116-12 for local network 104-1, and so on).

Examples of local networks 104 include home networks, personal area networks, business or school-based networks, Wi-Fi-enabled networks, Bluetooth-enabled networks, or combination thereof. Each local network 104 may use a variety of connectivity protocols (e.g., bus technology, ring technology, star technology, mesh technology). Each local network includes a plurality of network-connected devices 116. In some implementations, the collection of network-connected devices in communication with each local network communicate with the network 102 through a single network linking device. For example, a network-connected device 116-13 in a local network 104-1 can only communicate with the network 102 through the network linking device 110-1. Additionally, the collection of network-connected devices in communication with each local network may have a specific amount of total bandwidth for communication at a given time. Another implementation may include a set of sub-networks in communication with a local network, each through a respective network linking device.

A network-connected device 116 is an electronic device capable of requesting and receiving data over the local network 104 and the network 102. Example network-connected devices 116 include personal computers, mobile communication devices, entertainment centers (e.g., gaming systems), Internet-of-Things (IoT) network-connected devices such as appliances (e.g., refrigerators, washing machines, coffee makers), medical devices (e.g., pacemakers, glucose monitors), building-monitoring devices (e.g., thermostats, security systems, cameras, smoke detectors), and other devices that can send and receive data over a local network 104 and the network 102.

Each network-connected device 116 in a local network generates data traffic for its communications. The data traffic can include requests, heartbeat packets, responses to requests, streaming data, and the like, depending on the device being used. For example, a home monitoring device with a camera and microphone may provide audio and video data. Conversely, a thermostat may generate temperature and humidity reporting data. Thus, depending on the network device type, the amount and frequency of data that is generated and transmitted over data traffic for each device may vary significantly.

The amount of data traffic for a particular device can depend on the send/receive activity of the particular device. Depending on the total bandwidth available for a local network 104, the devices 116 may, at times, be competing for network bandwidth. Moreover, the percentage of total bandwidth used by a particular device relative to the other devices in the local network will vary over time or vary according to a time-dependent schedule. For example, a gaming device may have very little use during the workday in a home network, but during the evenings and on weekends, the gaming device may generate a relatively large amount of network traffic for the local network 104.

Because of network traffic constraints, there are times when traffic from two or more competing devices should be handled according to a prioritization scheme. For example, data traffic for security devices and medical monitoring in a local network should have priority over a gaming device in the same local network. Moreover, the prioritization of data traffic for each device may shift during the course of a day, week or another time period. For example, prioritizing network traffic for a credit card reader in a home business local network during business weekday business hours. Many users, however, do not know how to prioritize network traffic, and even if they did, they may not want to develop multiple schemes that can be applied at different times. Moreover, for a given set of a network devices, an optimum prioritization scheme may not be readily apparent; a user may have to try multiple different priority schemes before the handling of network traffic over a particular network 104 is improved. An automated network traffic prioritization system 120 addresses the technical problem of developing a prioritization scheme for network devices using machine learning technique.

Automated Network Traffic Prioritization System

The automated network traffic prioritization system 120 includes a traffic data collector 122 and a model generator 124 to train the model 130. The system 120, for multiple different local networks, collects traffic data 126 that represents communication traffic for network-connected devices 116. In some implementations, the system 120 is hosted on one or more computers in communication with the network 102. The data collected by the traffic data collector 122 is used by the model generator 124 to train the model 130.

The traffic data collector 122 collects data traffic and device types for each network-connected device in local networks 104. Each local network may be set up as a test network for data collection. Alternatively, each local network may be an actual local network at a particular location. In the case of the latter, users of each local network 104 may be requested to "opt in" so that their data may be collected by the traffic data collector 122. Each local network 104-1, 104-2, . . . 104-N is connected to the network 102 through respective network linking devices 110-1, 110-2, . . . 110-N. The traffic data collector 122 receives traffic data information from each of the plurality of network-connected devices 116 and device types for each of the network connected devices.

Traffic can also be aggregated by device type and independent of the local networks in which a device is deployed. This allows for the determination of device traffic behavior that is independent of the network topology of the particular network in which a device is deployed. Such signals can also be used as inputs for training a device prioritization model.

The traffic data collected by traffic data collector 122 can also include data that describes the service level of each local network 104, such as bandwidth usage, bandwidth capability, latency, turn-around window (the maximum time for a response to a message), number or frequency of errors in communication of data, and the like. In some implementations, the data collected by the traffic data collector 122 can span a period of time that includes all dayparts and multiple days, weeks, and even months.

For each network connected device 116, the system may also collect a corresponding device type. Examples of device types include health monitoring devices, security devices, entertainment devices, business operations devices, and the like. For example, a particular device may be a heart monitoring device, and thus may be of a device type of "health monitoring." Another device may be a coffee maker, and thus may be of a device type of "kitchen appliance," and so on.

A device type may be assigned to a device in a variety of ways. For example, a manufacturer of the device may assign a device type to the device, and the device may report its device type in response to a query. In situations where the device type is not assigned, the system 120 may determine the device type based on the traffic from the device, from traffic destinations, and so on. For example, a device that sends traffic to and receives traffic from a video service may be determined to be a video presentation device, while a device that sends data to and receives data from a health monitoring service may be determined to be a health monitoring device. The system 120 may, for example, have access to a mapping of network address and device types. Additionally, a user of the network-connected device may manually designate a device type to the device.

Using the data collected by the data traffic collector 122, the model generator 124 trains the device prioritization model 130. The model generator 124 may implement any appropriate machine learning process to train a model that receives, as input, a list of devices that are connected to a local network 104 and that generates, as output, one or more device prioritization schemes for the devices. Each device prioritization scheme optimizes device priority for traffic for a particular time period.

Model Training

Figure 2:
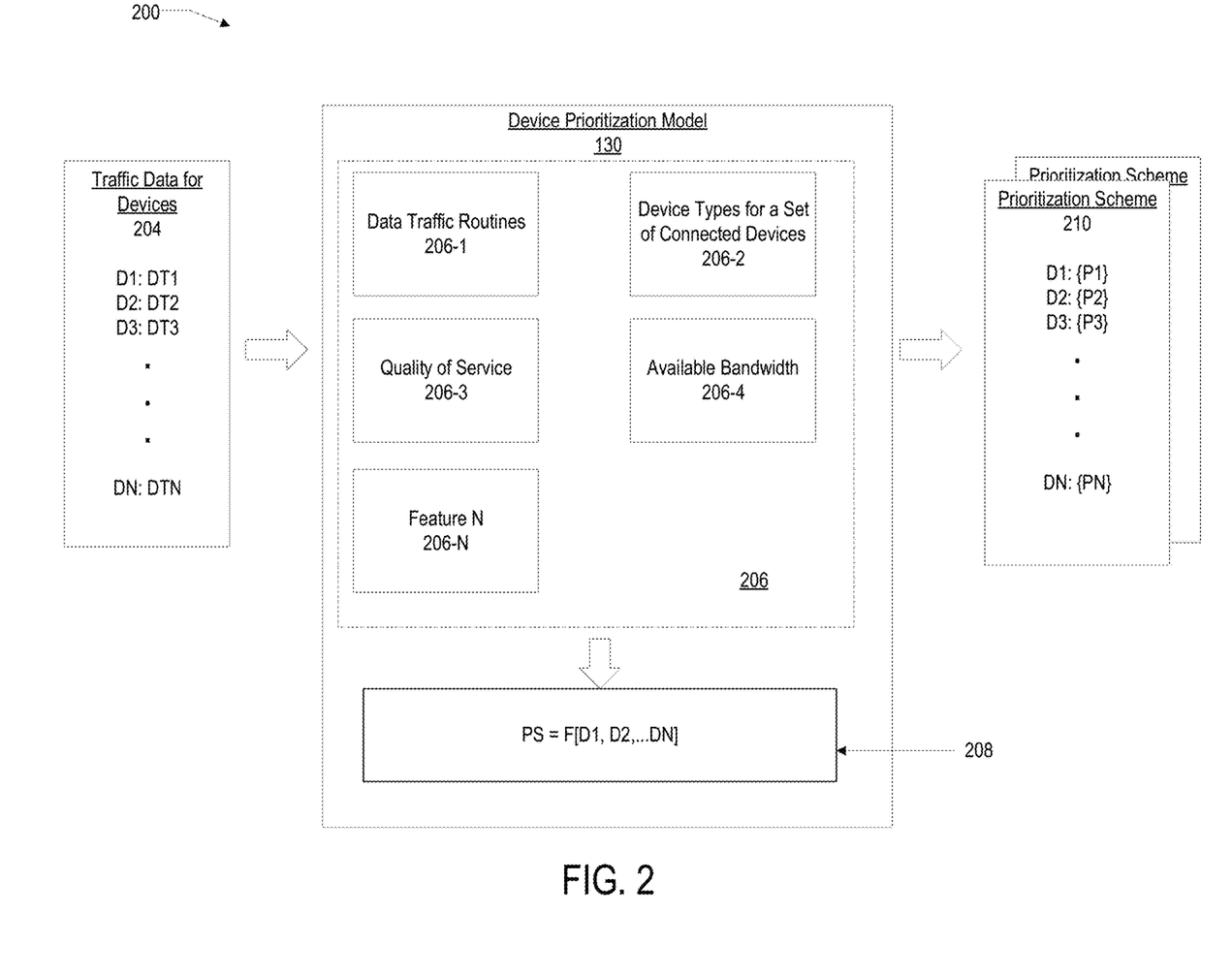
FIG. 2 is a diagram showing an example training process for a device prioritization model using traffic data from sets of network-connected devices on respective local networks.

FIG. 2 is a diagram showing an example training process for a device prioritization model 130 using traffic data from sets of network-connected devices on respective local networks. For each device Dx, corresponding device traffic data DTx is observed and collected by the traffic data collector 122. The device prioritization model 130 is trained using data collected by the traffic data collector 122.

Training of the device prioritization model 130 may incorporate one or more features 206 for producing a prioritization scheme function (PS) 208. Examples of features in the device prioritization model may include data traffic routines 206-1, device types for a set of connected devices 206-2, quality of service 206-3, available network bandwidth 206-4, and the like. This example list is not exhaustive, and any appropriate traffic prioritization feature may be used.

Data traffic routines 206-1 describe the traffic routines of each device on a network. Data traffic routines 206-1 may be determined in several ways. One way is by devices reporting their presence and type and using the reported device type to access data describing known traffic patterns for devices. For example, data traffic patterns for a particular thermostat may have already been provided to the traffic data collector 122. Thus, when the particular thermostat announces itself within a network, the traffic data collector 122 need only access the described data traffic routines 206-1.

Data traffic routines 206-1 may also be learned through observation. For example, some devices may send periodic heart beat signals, while other devices many only send data when queried. There periodicity of traffic for each device and the type of traffic for each device may be stored in the traffic routine data 206-1. Additionally, data traffic routines 206-1 may include data describing the periods of peak bandwidth usage for each device of a device type for a local network. For example, a data traffic routine for a credit card reader in a home business would include information about the hours and days of the week in which it produced highest data traffic, e.g., during the business hours of a workday, as well as information of when it produced minimal data traffic, e.g., during evening and weekend hours.

Another feature that may be used to train the device prioritization model 130 are the devices and device types for each set of network-connected devices 206-2. Device types may designate the importance of the data traffic for a particular network-connected device, or designate the functionality of the device. For example, a device type for a medical monitoring device (e.g., pacemaker) would identify the data traffic for the medical monitoring device as high importance in the model relative to a device type of a kitchen appliance. Furthermore, the different functions performed by the pacemaker, for example a "system working" handshake alert or a "emergency" device failure alert could further distinguish the importance of the device.

Training the device prioritization model 130 may also utilize quality of service measures 206-3 for each network device in a local network as a training feature. A quality of service measure may include, for example, allowable frequency of packet error or dropped packets, latency, jitter, data transfer speeds, and the like. The quality of service measure for a network device may apply for the network device for a set period of time. For example, a high quality of service measure could be applied to a gaming system during evenings and weekends when latency and jitter would interfere with the performance of the system.

Additionally, the device prioritization model 130 may be trained based on available bandwidth 206-4 for a local network. For networks with variability in bandwidth, such as those that slow down or have bandwidth caps at peak usage hours, the model may further be trained to incorporate this feature.

Other features 206-N may also be used to train the model. For example, the sensitivity of a device in response to a traffic error, e.g., a dropped packet or high traffic latency, may be a feature that is used in training a model. To illustrate, a first device may be observed to often crash when traffic for the device is dropped; conversely, a second device may be quite robust to traffic errors and never crashes in response to traffic errors. Accordingly, the model that is trained may tend to prioritize the first device over the second device (absent other factors) so as to reduce the likelihood that the prioritization scheme affects traffic to the point that the first device experiences system errors.

Another feature is user satisfaction. Once prioritization schemes are deployed, the system may monitor for changes to the prioritizations schemes by the users, and/or receive user feedback regarding the prioritization schemes. In the case of the former, common changes to particular schemes may be interpreted as negative feedback, and the changes to the schemes can be used to re-train the model periodically. In the case of the latter, user feedback can be used to validate prioritization schemes or be interpreted as negative feedback, depending on the feedback.

Each device with an assigned device type also has at least one device priority value. Each device priority value designates an importance of the device traffic relative to traffic from other devices connected to a local network. In some implementations, default device priority values can be assigned by the device manufacturer based on the device type of the device. For a device in a local network, the device priority value assigned to the device may be used as a priority value for determining traffic prioritization for the device. For example, a manufacturer of a heart monitoring device may assign a device priority value to the heart monitoring device such that traffic from the heart monitoring device in a local network is high priority relative to the traffic from other devices in the local network.

Device priority values may also be defined by the system 120 instead of the manufacturer. For example, the system 120 may have a mapping of device types to device priority values. Other ways of determining device priority values may also be used.

The model generator 124, in some implementations, may be trained to generate a prioritization scheme based the device priority value and prioritize all traffic for a device, regardless of type, the same. For example, a response packet to a ping from health monitoring device may the same priority as a reporting message from the health monitoring device that reports a medical event.

In other implementations, the model 130 may be trained to provide a more granular prioritization for device traffic based on a type of traffic. The granular prioritization is realized by use of different traffic priority values for a device. The traffic priority value assigned to a particular traffic item for a device may depend on the function to which the traffic item relates. For example, for a network-connected pacemaker device in a local network, the pacemaker device may have multiple traffic priority values for traffic, depending on the type of function to which the traffic relates. Traffic for a normal status update check signaling "device working" may have a traffic priority value of 3 (on a scale of 10), indicating a relatively low priority for the particular traffic data for the status update check, whereas traffic an alarm status update signaling "device malfunctioning" may have a traffic priority value of 10 out of 10, indicating high priority for the particular traffic data for the alarm status.

The device prioritization model 130 may, in some implementations, includes weights for the traffic based on each device type and each respective device priority value. Moreover, the model may be trained for one or more prioritization scheme objectives, and the weights may differ for each objective.

A trained device prioritization model 130 yields a prioritization scheme function (PS) 208. In general, the leaned function is of the form:

$$PS=F[D1, D2, \ldots DN]$$

Where:
D1, D2, . . . DN are a set of devices input to the function;
F[D1, D2, . . . DN] is a learned function of the model 130; and
PS is the priority scheme (or set of priority schemes) for the set of devices D1, D2, . . . DN.

The device prioritization scheme function 208 of the model 130 receives, as input, a set of network connected devices 204 in a local network. The output of the device prioritization scheme function includes at least one prioritization scheme 210. In implementations in which traffic priority values are not used, the prioritization scheme prioritizes traffic on a device-by-device basis for a set of devices. In implementations in which traffic priority values are used, however, the prioritization scheme includes at least one traffic priority value P for each of the network connected devices. Sets of traffic prioritization values for devices Dx are indicated by corresponding sets {Px} in the example prioritization scheme 210 of FIG. 2.

Figure 3:
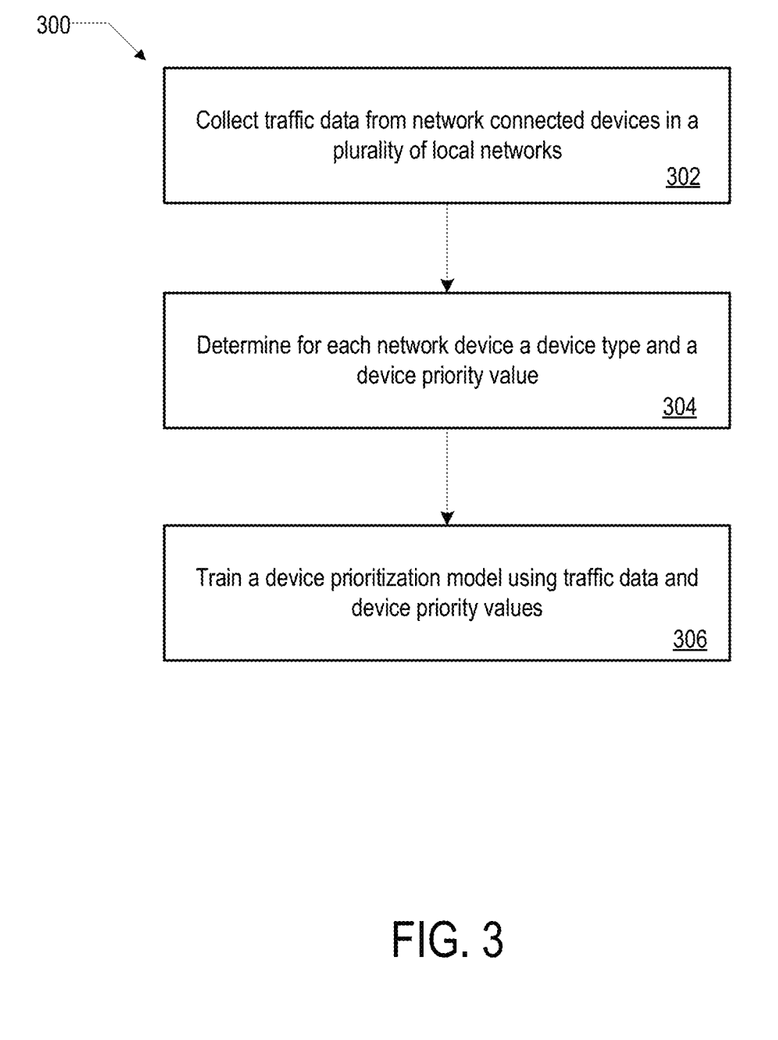
FIG. 3 is a flow chart of an example process for training a prioritization model.

FIG. 3 is a flow chart of an example process 300 for training a prioritization model 130. The process 300 is implemented in one or more computers.

A system collects traffic data from network connected devices in a plurality of local networks (302). As described above, local networks 104-1, 104-2 . . . 104-N may each have unique configurations of network connected devices 116 in each local network communicating with the network 102 through respective network linking devices (e.g., local network routers) 110-1, 110-2 . . . 110-N. The traffic data 126 from each network connected device 116 is collected by a traffic data collector 122 (302).

The system determines a device type for each network connected device and device priority values (304). The device types may be included in the traffic packets, or may be derived by examining packet destinations, as described above. For example, a device type may be determined for a credit card reader based on the destination or source of the traffic data for the credit card reader (e.g., commerce or banking websites, credit card companies). In another example, a heart rate monitor may be sending updates to emergency medical personnel (e.g., 911) or to a medical facility (e.g., primary care provider).

The device priority values designate an importance of the device traffic relative to traffic from other devices connected to a local network. As noted above, the device priority values can be assigned based on, in part, the device type. For example, a home security system may have an assigned high device priority value for its traffic relative to the traffic of other devices in the same local network.

The device prioritization model 130 is trained using traffic data and device priority values (306). The device prioritization model 130 may include at least one of a set of features 206 describe above, such as data traffic routines, quality of service, device types, and available bandwidth. For example, a device prioritization model 130 made factor in a set of features including thresholds for quality of service for each device type and bandwidth caps for each device type or device function.

Once trained, the device prioritization model 130 can receive information about a set of traffic data for devices 204 in a local network as input and output at least one prioritization scheme 210. Each prioritization scheme 210 includes optimized device bandwidth allocation parameters, comprising at least one or more traffic priority values $P_N$ for each network connected device $D_N$. For example, a prioritization scheme applied to a local network with the following devices: a coffeemaker, a credit card reader, and a security system. The prioritization scheme could include multiple traffic priority values for each of the devices. For a security system having two types of alerts, one "normal operation" and one "emergency situation," the traffic from the "normal operation" may be assigned a lower traffic priority value by the prioritization scheme, while the "emergency situation" may be assigned a higher traffic priority value by the prioritization scheme. The lower and higher traffic priority values assigned to the security system are relative to the traffic priority values of the other devices (e.g., the coffee maker and the credit card reader) which each have at least one traffic priority value assigned by the prioritization scheme.

Each local network in communication with a set of network-connected devices has at least one prioritization scheme for the set of network-connected devices. In some implementations, multiple prioritizations schemes may be generated for a same set of network-connected devices. For example, in the above mentioned local network including a coffeemaker, a credit card reader, and a security system: a first prioritization scheme may be applied to a local network 104 for weekdays during business hours, and a second, different prioritization scheme may be applied to the same local network 104 for weekday evenings and weekends.

In some implementations, the device prioritization model may determine multiple time-dependent prioritization sub-schemes for a set of network-connected devices in a local network, such that each time-dependent sub-scheme is optimized for a particular time period with corresponding network device traffic data. For example, for a set of network-connected devices comprising a coffee-maker, a credit card reader, and a gaming system, multiple time-dependent sub-schemes may be applied. A first time-dependent sub-scheme may prioritize the credit card reader over the other devices during business hours and on weekdays. A second time-dependent sub-scheme may prioritize the gaming system over the other devices during evenings and weekends.

In some implementations, the traffic priority value of a network-connected device for performing particular function may be variable, such that the traffic priority value may change over time, or may vary temporally on a particular schedule. The traffic priority value may vary for different prioritization schemes, between prioritization sub-schemes, or within the same prioritization scheme as applied over a time period. For example, the traffic priority value for playing an online game on a gaming system may be a high traffic priority value (e.g., 8 out of 10) during the evenings and weekends when it generates a large quantity of data traffic and delays in stream would be detrimental to its performance. However, the traffic priority value for playing the online game on the gaming system may be a low traffic priority value (e.g., 2 out of 10) during normal business hours when it is not in use and generates low quantity of data traffic.

In addition to assigning traffic priority values to a set of network devices, a prioritization scheme may also include a quality of service cap, wherein the network devices cannot exceed the quality of service cap for a prioritization scheme. This could be implemented in multiple forms, including bandwidth allocation caps, or wherein minimum and maximum bandwidth allocation parameters can be assigned to each network connected device. The quality of service cap may change based on the prioritization scheme applied to the local network and/or the set of network connected devices in the local network. For example, if a local network includes a single network connected device, the prioritization scheme may not assign a quality of service cap to the single device.

The prioritization schemes can furthermore be used to weight the importance of the quality of service for each network connected device. For example, a quality of service cap set for a coffee maker in a local network with multiple other network connected devices would prevent the traffic priority value assigned to the coffee maker from exceeding a certain level, (e.g., 7 out of 10) relative to the other network connected devices in the local network. A quality of service cap implemented in this instance would furthermore prevent a low impact or low importance device (the coffee-maker) that may have relatively high data traffic needs from dominating a local network.

Additionally, in some implementations, particular devices may have bandwidth prioritization cap that applies a first traffic priority value for a first portion of bandwidth and a second traffic priority value for a second portion of bandwidth. For example, a video streaming device may be allocated a first priority value for a first percentage of overall bandwidth, and, should the video streaming device exceed the bandwidth, its remaining traffic is allocated a second value that is lower than the first. Such a bandwidth prioritization cap scheme tends to preclude any one device from becoming a "greedy" device should its traffic demands spike for any particular reason.

Moreover, in additional implementations, the prioritization scheme may be applied to an overall percentage of bandwidth, and a certain amount of bandwidth "headroom" may be preserved. For example, assume that a total bandwidth is 100 Mbs. The bandwidth prioritization caps of all devices may, in the aggregate, not exceed 95% of the total bandwidth, thus reserving 5 Mbs of "prioritized" traffic. This is useful for when headroom is needed, such as when new devices join the network and are not subject to the prioritization scheme. Thus, rather than relegating the new device to a lowest priority, the prioritization scheme allows for at least some bandwidth that can be used by the new device outside of a prioritization scheme.

Applying a Prioritization Scheme to a Local Network

Figure 4:
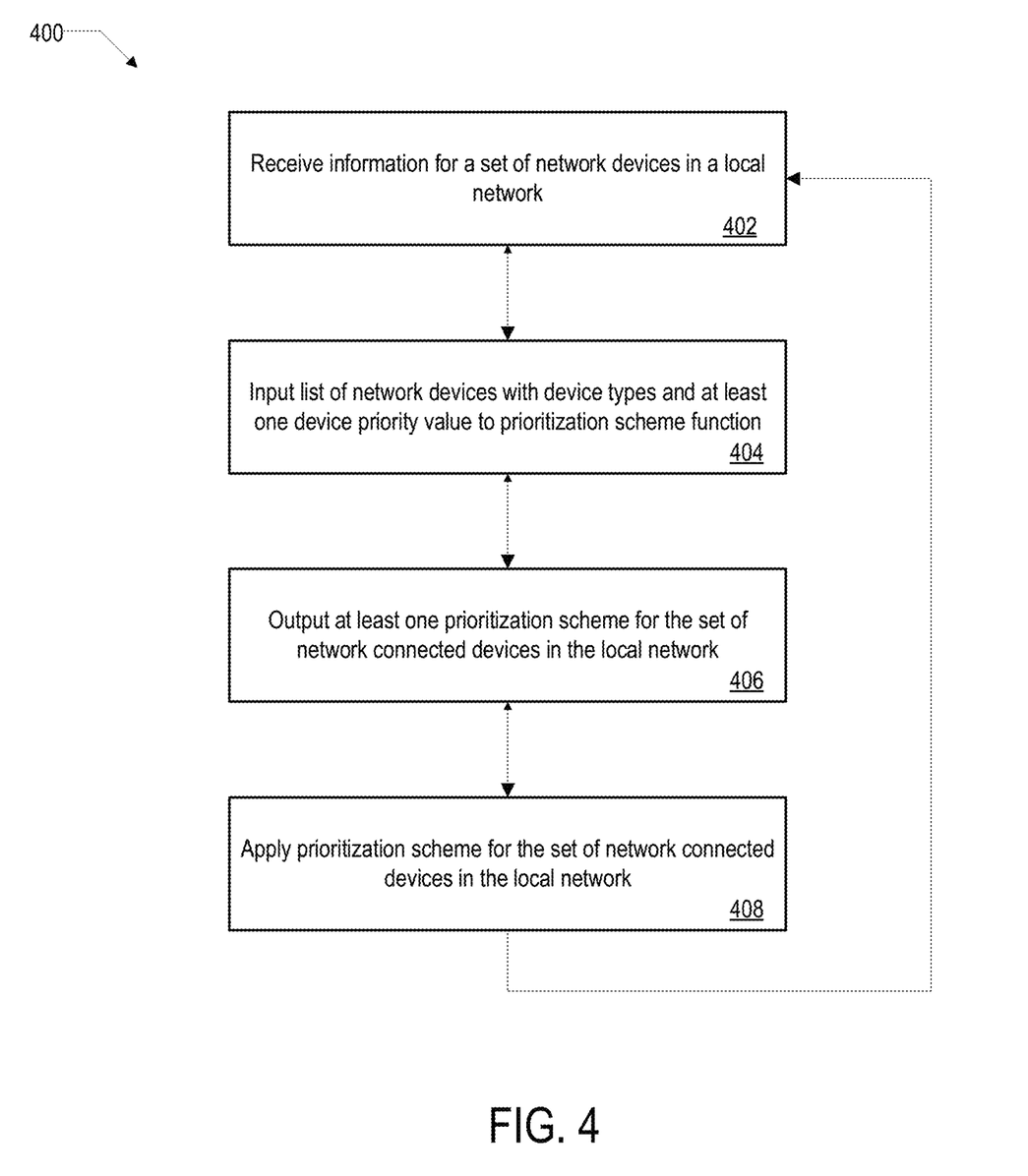
FIG. 4 is a flow chart of an example process for applying a prioritization scheme to a local network.

FIG. 4 is a flow chart 400 of an example process for applying a prioritization scheme to a local network. For a trained device prioritization model 130, having a prioritization scheme function 208, the system receives information about a set of network connected devices 204 in a local network (402). For example, a local network including a glucose monitor, a network-connected washing machine, and an entertainment system for streaming content. Each of the devices has a device type (e.g., medical device, appliance, and media device, respectively) and each of the devices has a device priority values based on the device type (e.g., medical device has a high device priority value, appliance has a low priority value, and media device has a medium device priority value).

The set of network connected devices each with an assigned device type and at least one or more device priority values is inputted to the device prioritization scheme function (404). For example, the input list for the above-mentioned example includes: medical device/high device priority value, appliance/low device priority value, and media device/medium device priority value. The device priority values can be rated on many different scaling systems including a rating of X out of Y (e.g., 3 out of 10), threshold levels (e.g., low/medium/high), or the like.

From the input list, the model 130 outputs at least one prioritization scheme for the set of network connected devices in the local network (406). A prioritization scheme output includes for each device in the local network at least one traffic priority value. For example, the glucose monitor may have a single device priority value of 10 out of 10 based on the "medical device" classification. However, the prioritization scheme may assign two traffic priority values: a low traffic priority value 2 out of 10 for "routine check in" alerts from the glucose monitor and a high traffic priority value 10 out of 10 for "emergency" alerts from the glucose monitor.

The one or more prioritization schemes are applied to the set of network connected devices in the local network (408). As mentioned above, multiple prioritization schemes can be applied to a local network. For example, the different prioritization schemes may be optimized for device traffic at different time periods (e.g., a first for business hours on weekdays and a second for evenings and weekends).

The device prioritization model may further comprise a time-delay for automatically adjusting or updating a prioritization scheme for adding or removing one of a set of network connected devices in a local network. The time-delay can take many forms, for example, the time-delay may be based on a difference in time between when a network device was added or removed to the local network and when the prioritization scheme was applied to the local network. An advantage of a time-delay would be to prevent the applied prioritization scheme from changing for a transitory device, such as a guest mobile device in a local network.

A time-delay could also be variable based on the device type or device priority values of an added device to the local network. For example, if a glucose monitor is added to a local network, the time-delay would be much shorter for adjusting or updating the prioritization scheme than if a coffee maker is added to the same local network, because of the difference in critical functionality of the two devices.

Furthermore, a device prioritization model 130 may also have an adjustable sensitivity to retraining. A threshold for retraining could prevent retraining the prioritization model based on exceptional cases. Exceptional cases may include but are not limited to: (a) errant or malfunctioning devices in local networks, (b) local networks with unusual bandwidth allocation demands, (c) local networks with unusual sets of devices or device traffic, or (d) a combination thereof. For example, for a local network including a security system and a second, redundant security system, may produce erroneous or unusual data traffic. Based on an adjustable sensitivity to the model, it may not be favorable for the automated network traffic prioritization system 120 to collect data from the two, redundant security systems in the local network.

While the examples above are described in a model that is learned over many networks, the system can be implemented on a smaller scale and in a local network. For example, in FIG. 1, each network linking device 110 may implement its own respective traffic data collector and model trainer, and may learn a model 130 based on the network traffic and devices observed in its own respective network 104.

Additional Implementation Details

Figure 5:
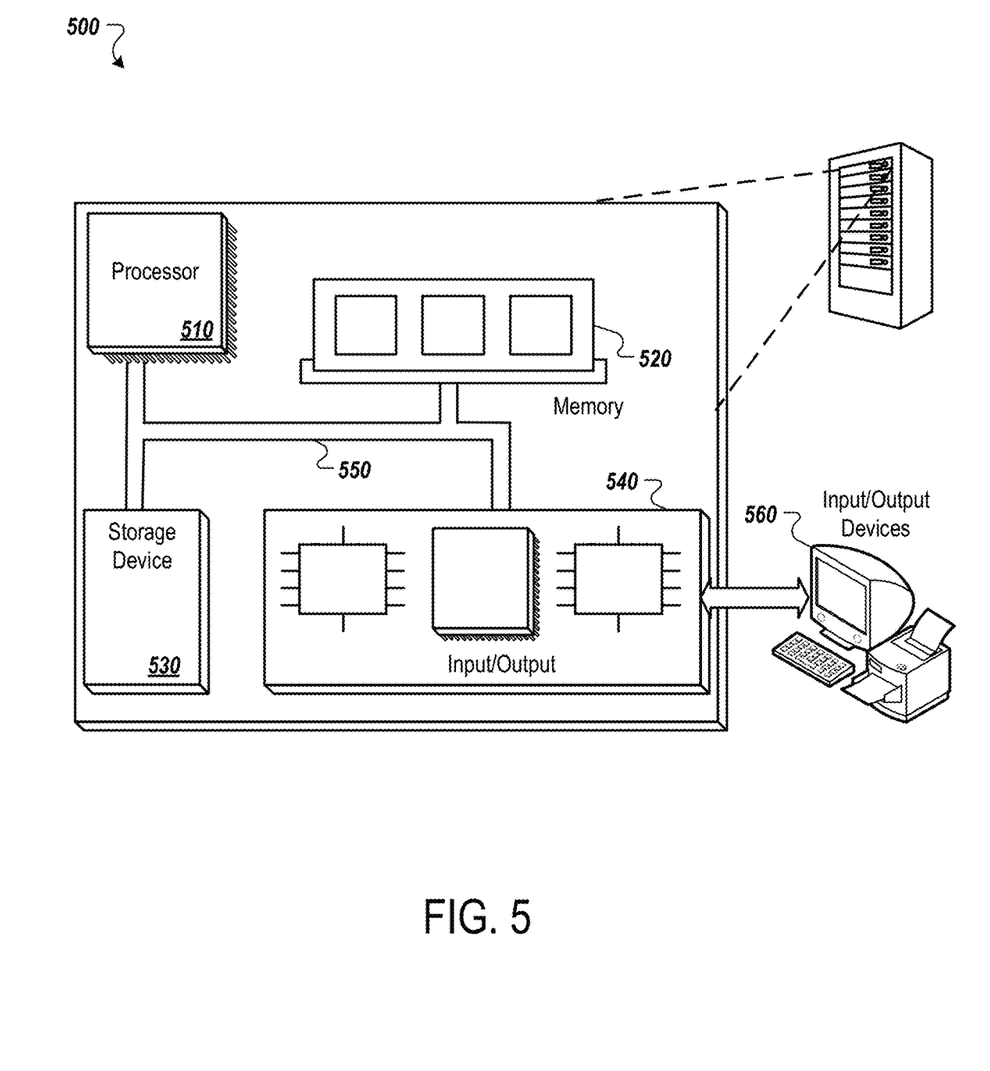
FIG. 5 is a block diagram of an example computer system.

FIG. 5 is block diagram of an example computer system 500 that can be used to perform operations described above. The system 500 includes a processor 510, a memory 520, a storage device 530, and an input/output 540. Each of the components 510, 520, 530, and 540 can be interconnected, for example, using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 400. In one implementation, the storage device 530 is a computer-readable medium. In various different implementations, the storage device 530 can include, for example, a hard disk device, an optical disk device, a storage device that is shared over a network by multiple computing devices (e.g., a cloud storage device), or some other large capacity storage device.

The input/output device 540 provides input/output operations for the system 400. In one implementation, the input/output device 540 can include one or more of a network interface device, e.g., an Ethernet card, a serial communication device, e.g., and RS-232 port, and/or a wireless interface device, e.g., and 802.11 card. In another implementation, the input/output device can include driver devices configured to receive input data and send output data to other input/output devices, e.g., keyboard, printer and display devices 560. Other implementations, however, can also be used, such as mobile computing devices, mobile communication devices, set-top box television client devices, etc.

Although an example processing system has been described in FIG. 5, implementations of the subject matter and the functional operations described in this specification can be implemented in other types of digital electronic circuitry, or in computer software, firmware, or hardware, including the structures disclosed in this specification and their structural equivalents, or in combinations of one or more of them.

In situations in which the systems discussed here collect personal information about users, or may make use of personal information, the users may be provided with an opportunity to control whether applications or features collect user information (e.g., information about a user's social network, social actions or activities, profession, a user's preferences, or a user's current location), or to control whether and/or how to receive content that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a user computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any features or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method, comprising:
receiving a device prioritization scheme for a particular list of network devices that prioritizes device traffic among the particular list of network devices, the device prioritization scheme comprising:
a first set of device priority values for the list of network devices that prioritizes device traffic among the list of network devices for an emergency situation; and
a second set of device priority values for the list of network devices that prioritizes device traffic among the list of network devices for a non-emergency situation,
wherein at least one device priority value of the first set of device priority values for a given network device of the list of network devices is different for the emergency situation than the device priority value of the second set of device priority values for the given network device for the non-emergency situation, and
wherein each device priority value is a measure of a priority for device traffic for each network device relative to each other device traffic of other network devices in the list of network devices; and
applying, to the particular local network including the particular list of network devices, the prioritization scheme for prioritizing device traffic among the particular list of network devices, the applying comprising:
determining if an emergency or non-emergency situation applies;
in response to determining the emergency situation applies, applying the first set of device priority values to the list of network devices: and
in response to determining the non-emergency situation applies, applying the second set of device priority values to the list of network devices.

2. The method of claim 1, wherein the device prioritization scheme for the particular list of network devices that prioritizes device traffic among the particular list of network devices is generated by a machine-learned device prioritization model, wherein the generating comprises:
providing, to the machine-learned device prioritization model, the particular list of network devices and device types for each network device of the list of network devices connected to the particular local network.

3. The method of claim 1, wherein the first set of device priority values and the second set of device priority values for the list of network devices are based on the device type of each of the network devices.

4. The method of claim 1, wherein the device priority value of the first set of device priority values for the given network device of the list of network devices is higher priority for the emergency situation than the device priority value of the second set of device priority values for the given network device for the non-emergency situation.

5. The method of claim 1, wherein the prioritization scheme comprises a bandwidth prioritization cap that applies a first traffic priority value for a first portion of bandwidth used by the network device and a second traffic priority value for a second portion of bandwidth used by the network device.

6. The method of claim 5, wherein the prioritization scheme comprises a first bandwidth cap for a first device function and a second, different bandwidth cap for a second device function for the network device.

7. A system, comprising:
a data processing apparatus that includes one or more processors; and
a computer storage medium in data communication with the data processing apparatus and encoded instructions defining:

a traffic data collector that, when executed by the data processing apparatus, causes the data processing apparatus to perform operations comprising:

receiving a device prioritization scheme for a particular list of network devices that prioritizes device traffic among the particular list of network devices, the device prioritization scheme comprising:
- a first set of device priority values for the list of network devices that prioritizes device traffic among the list of network devices for an emergency situation; and
- a second set of device priority values for the list of network devices that prioritizes device traffic among the list of network devices for a non-emergency situation,
- wherein at least one device priority value of the first set of device priority values for a given network device of the list of network devices is different for the emergency situation than the device priority value of the second set of device priority values for the given network device for the non-emergency situation, and
- wherein each device priority value is a measure of a priority for device traffic for each network device relative to each other device traffic of other network devices in the list of network devices; and applying, to the particular local network including the particular list of network devices, the prioritization scheme for prioritizing device traffic among the particular list of network devices, the applying comprising:
- determining if an emergency or non-emergency situation applies;
- in response to determining the emergency situation applies, applying the first set of device priority values to the list of network devices: and
- in response to determining the non-emergency situation applies, applying the second set of device priority values to the list of network devices.

8. The system of claim 7, wherein the device prioritization scheme for the particular list of network devices that prioritizes device traffic among the particular list of network devices is generated by a machine-learned device prioritization model, wherein the generating comprises:
providing, to the machine-learned device prioritization model, the particular list of network devices and device types for each network device of the list of network devices connected to the particular local network.

9. The system of claim 7, wherein the first set of device priority values and the second set of device priority values for the list of network devices are based on the device type of each of the network devices.

10. The system of claim 7, wherein the device priority value of the first set of device priority values for the given network device of the list of network devices is higher priority for the emergency situation than the device priority value of the second set of device priority values for the given network device for the non-emergency situation.

11. The system of claim 7, wherein the prioritization scheme comprises a bandwidth prioritization cap that applies a first traffic priority value for a first portion of bandwidth used by the network device and a second traffic priority value for a second portion of bandwidth used by the network device.

12. The system of claim 11, wherein the prioritization scheme comprises a first bandwidth cap for a first device function and a second, different bandwidth cap for a second device function for the network device.

13. A non-transitory computer storage medium storing instructions executable by a data processing apparatus and that upon such execution cause the data processing apparatus to perform operations comprising:

receiving a device prioritization scheme for a particular list of network devices that prioritizes device traffic among the particular list of network devices, the device prioritization scheme comprising:
- a first set of device priority values for the list of network devices that prioritizes device traffic among the list of network devices for an emergency situation; and
- a second set of device priority values for the list of network devices that prioritizes device traffic among the list of network devices for a non-emergency situation,
- wherein at least one device priority value of the first set of device priority values for a given network device of the list of network devices is different for the emergency situation than the device priority value of the second set of device priority values for the given network device for the non-emergency situation, and
- wherein each device priority value is a measure of a priority for device traffic for each network device relative to each other device traffic of other network devices in the list of network devices; and applying, to the particular local network including the particular list of network devices, the prioritization scheme for prioritizing device traffic among the particular list of network devices, the applying comprising:
- determining if an emergency or non-emergency situation applies;
- in response to determining the emergency situation applies, applying the first set of device priority values to the list of network devices: and
- in response to determining the non-emergency situation applies, applying the second set of device priority values to the list of network devices.

14. The computer storage medium of claim 13, wherein the device prioritization scheme for the particular list of network devices that prioritizes device traffic among the particular list of network devices is generated by a machine-learned device prioritization model, wherein the generating comprises:
providing, to the machine-learned device prioritization model, the particular list of network devices and device types for each network device of the list of network devices connected to the particular local network.

15. The computer storage medium of claim 13, wherein the first set of device priority values and the second set of device priority values for the list of network devices are based on the device type of each of the network devices.

16. The computer storage medium of claim 13, wherein the device priority value of the first set of device priority values for the given network device of the list of network devices is higher priority for the emergency situation than the device priority value of the second set of device priority values for the given network device for the non-emergency situation.

17. The computer storage medium of claim 13, wherein the prioritization scheme comprises a bandwidth prioritization cap that applies a first traffic priority value for a first portion of bandwidth used by the network device and a second traffic priority value for a second portion of bandwidth used by the network device.

18. The computer storage medium of claim 17, wherein the prioritization scheme comprises a first bandwidth cap for a first device function and a second, different bandwidth cap for a second device function for the network device.

* * * * *